United States Patent [19]
Pologe

[11] Patent Number: 5,891,022
[45] Date of Patent: Apr. 6, 1999

[54] APPARATUS FOR PERFORMING MULTIWAVELENGTH PHOTOPLETHYSMOGRAPHY

[75] Inventor: Jonas A. Pologe, Boulder, Colo.

[73] Assignee: Ohmeda Inc., Louisville, Colo.

[21] Appl. No.: 719,601

[22] Filed: Sep. 25, 1996

[51] Int. Cl.$^6$ ........................................................ A61B 5/00
[52] U.S. Cl. .......................... 600/323; 600/310; 600/322; 600/326; 600/473
[58] Field of Search ............................... 128/633, 664–7, 128/634; 359/114, 124; 356/39–41; 600/310, 314–316, 322–324, 326, 328, 340

[56] References Cited

U.S. PATENT DOCUMENTS

| | | | |
|---|---|---|---|
| 4,543,961 | 10/1985 | Brown | 128/667 |
| 4,936,679 | 6/1990 | Mersch | 356/41 |
| 5,271,079 | 12/1993 | Levinson | 385/46 |
| 5,304,495 | 4/1994 | Yim | 128/673 |
| 5,339,810 | 8/1994 | Ivers et al. | 128/664 |
| 5,355,880 | 10/1994 | Thomas et al. | 128/664 |
| 5,553,615 | 9/1996 | Carim et al. | 128/664 |

OTHER PUBLICATIONS

Powers, J.P., "An Intro to Fiber Optic Systems," Aksen Associates Incorporated Publishers, Boston, MA, 1993, pp. 156 & 399–406.

Primary Examiner—Michael Peffley
Assistant Examiner—Bryan K. Yarnell
Attorney, Agent, or Firm—Holme Roberts & Owen LLP

[57] ABSTRACT

A photoplethysmographic measurement device that utilizes wavelength division multiplexing is provided. Signals from multiple light emitters are combined into a single multiplexed light signal in a test unit before being delivered to a physically separated probe head attached to a test subject. The probe then causes the single multiplexed signal to be transmitted through a tissue under test on the test subject, after which it is processed to determine a blood analyte level of the test subject. By combining the light signals into a single multiplexed signal before delivering the signals to the probe, a single light guide, such as a single optical fiber, can be used to deliver the signals to the probe, thereby reducing system implementation cost and increasing the flexibility of the probe cable. In addition, the invention allows the signals from the light emitters to be directed into the test subject from a single point source, which can significantly increase measurement accuracy.

16 Claims, 3 Drawing Sheets

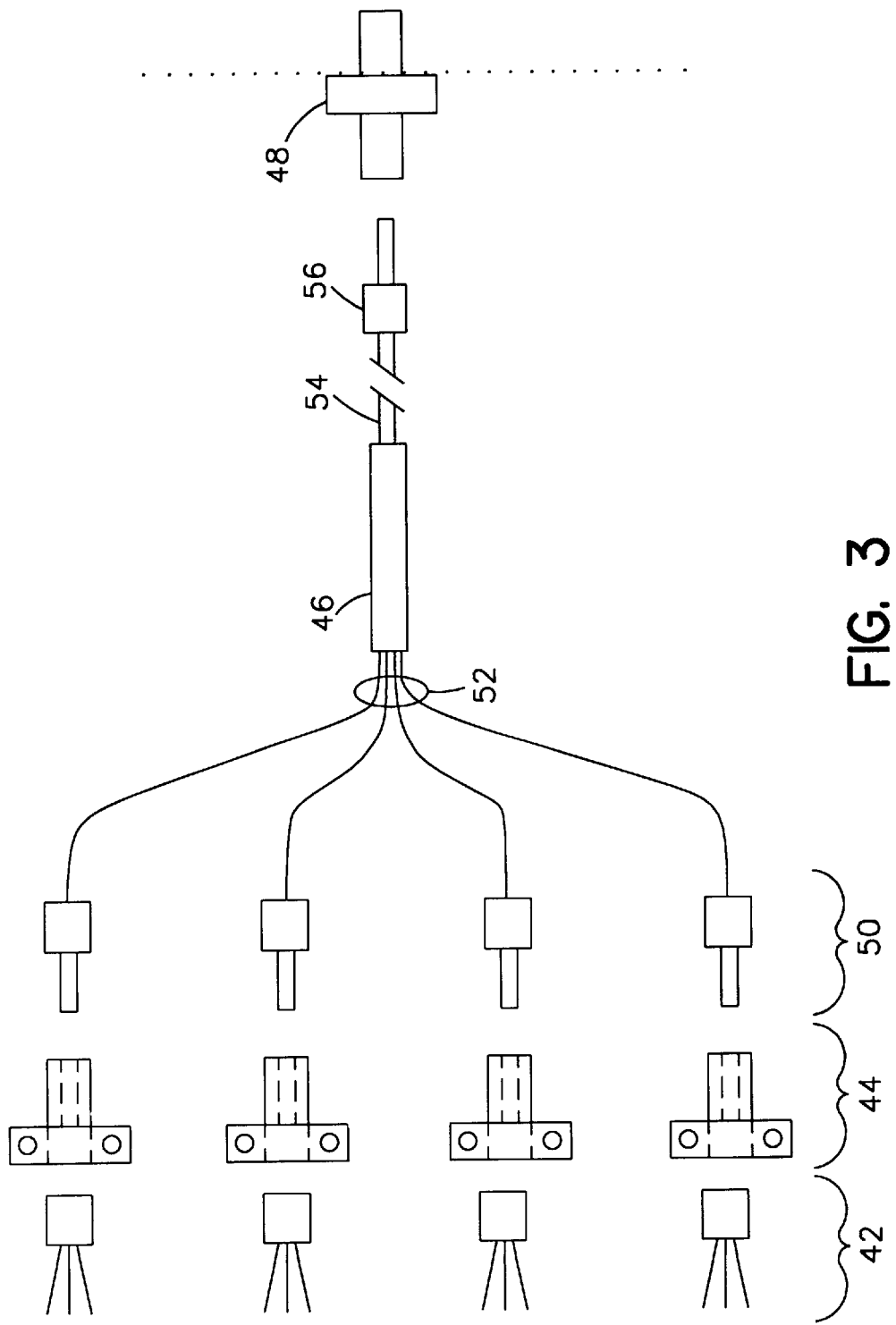

APPARATUS FOR PERFORMING MULTIWAVELENGTH PHOTOPLETHYSMOGRAPHY

FIELD OF THE INVENTION

The present invention relates in general to systems for performing photoplethysmographic measurements and is particularly apt for use in pulse oximetry systems.

BACKGROUND OF THE INVENTION

Photoplethysmography is a measurement technique that uses light pulses from different portions of the electromagnetic spectrum (i.e., relatively narrow band light pulses having different center wavelengths) to quantitatively and noninvasively measure various blood analytes in a test subject. The measurement is based on the difference in the light transmittance of the various blood analytes (such as oxyhemoglobin and reduced hemoglobin) of the test subject at the different wavelengths. One type of photoplethysmographic process, known as pulse oximetry, is used to measure the oxygen saturation level of a person's arterial blood. In a pulse oximetry system, pulses of light having different spectral contents and center wavelengths are directed into the tissue under test, such as a finger or an earlobe. Transmitted light pulses are then received on the other side of the tissue under test (or in the case of a reflectance measurement, a small distance away on the same side) and are processed by the pulse oximetry system to determine the oxygen saturation level of the person's arterial blood.

Pulse oximetry systems generally include a main test unit housing, among other things, the control circuitry for the system; a probe unit for attaching to the appropriate tissue during a test; and signal transmission means for delivering signals between the main test unit and the probe. The main test unit may comprise either a benchtop unit or a handheld unit and, as described above, generally includes the control circuitry for controlling the operation, timing, and display functions of the system. The main test unit may also include a display for displaying measurement results to a user, an input device allowing a user to set various monitoring parameters, and an audible alarm for, among other things, warning a user of potentially dangerous analyte levels.

The probe unit generally comprises means for directing light from various emitters into the tissue under test and means for receiving transmitted light from the tissue. The probe may also include means for converting the transmitted light into an electrical signal for processing purposes. Because medical applications require the maintenance of hygienic conditions, it is often desirable that probes be disposable. Disposable probes should be relatively inexpensive to produce. In addition, because a probe is in contact with a person's skin during operation, it is important that the probe remain relatively cool during operation to prevent burns. Further, because the path a light signal takes through the tissue under test can affect the accuracy of the measurement it is important that all light pulses be directed into the tissue from essentially a single point. Lastly, it is generally desirable that probes be relatively small and lightweight so that they are easier to handle and remain in a fixed position on the appendage throughout testing without the tendency to fall off.

The signal transmission means generally includes both means for delivering signals to the probe for use by the probe in directing light into the tissue under test and means for delivering a signal representative of the light transmitted through the tissue under test back to the main test unit. It is generally desirable that the signal transmission means be as lightweight and flexible as possible. Therefore, it is advantageous to reduce the number of signal carriers in the signal transmission means. In addition, because the signal transmission means must be replaced periodically, it is desirable that it be relatively inexpensive to produce.

SUMMARY OF THE INVENTION

It is an object of the present invention to provide a photoplethysmographic measurement system that utilizes wavelength division multiplexing (WDM) to deliver light pulses between a main test unit and a probe.

It is another object of the present invention to provide a photoplethysmographic measurement system that uses a single light guide to deliver light pulses from the main test unit to the probe.

It is still another object of the present invention to provide a photoplethysmographic measurement system that provides accurate and reliable measurements while being relatively inexpensive to manufacture and operate.

It is a further object of the present invention to provide a photoplethysmographic measurement system that uses a probe that is relatively inexpensive to manufacture and hence may be disposable.

It is a further object of the present invention to achieve the above described objects in a photoplethysmographic measurement system for determining a variety of arterial blood analytes.

To achieve the above objectives, a system is provided that utilizes wavelength division multiplexing to combine the output signals from multiple light sources (i.e., emitters) into a single multiplexed signal. Thereafter, a single optical transmission line, such as a fiber optic cable, a fiber bundle, or other light guiding means may be utilized between the main test unit and the probe to deliver all light pulses to the probe, regardless of the number of light sources being used. In addition, because all of the light pulses exist on a single transmission line, the light pulses may be directed from the probe into the tissue under test from a single point source, thereby eliminating measurement errors due to differing optical paths. Further, because the light sources are included in the main test unit, rather than the probe, the probe may be relatively lightweight, is not prone to heating, and is relatively inexpensive to produce, allowing it to be disposable.

In accordance with one aspect of the present invention, a photoplethysmographic measurement apparatus is provided having: a plurality of separate emitters, wherein each emitter produces a light signal having a unique spectral content; means for combining the light signals from the plurality of emitters into a single light signal; means for delivering the single light signal to the tissue so that the single light signal is directed into the tissue; means for receiving a transmitted light signal from the tissue, the transmitted light signal resulting from the transmission of the single light signal through the tissue; and means for processing the transmitted light signal to determine one or more blood analyte levels in the tissue.

In one embodiment, the combining means includes a coupler for coupling the output signals from the plurality of emitters onto a single output line, using wavelength division multiplexing (WDM). In addition, as in most modern pulse oximeters, the emitters are time division multiplexed. Thus the output line of the wavelength division multiplexed coupler is actually carrying the light from only one emitter at any one point in time. It should be noted that time division multiplexing of the emitters is not a requirement but has been found to simplify the design.

The plurality of separate emitters includes multiple separate light sources, such as light emitting diodes (LEDs) and laser diodes. In general, the signal delivery means includes a single input/single output light guide such as a single optical fiber, a single fiber bundle, or other type of light guiding means. The single input/single output light guide delivers light to a probe head which couples the light into the tissue under test. The probe head can also include detection means for converting the light signal transmitted through the tissue under test into an electrical signal. In one embodiment, the plurality of emitters and the combining unit are included in a housing, such as a bench top test unit or a handheld unit. The housing may also include means for communicating measurement results to users and means for receiving commands from users. The probe head is physically separated from the housing with the single input/single output light guide connecting them.

In another aspect of the present invention, a method is provided for photoplethysmographically measuring one or more arterial blood analytes. The method includes: providing a plurality of separate light signals, each light signal including a spectral content having a unique center frequency; combining the plurality of separate light signals into a single light signal; delivering, after the step of combining, the single light signal to the tissue so that the single light signal is directed into the tissue; detecting a transmitted light signal from the tissue; and processing the transmitted light signal to determine a blood analyte level for the tissue.

As described above, the plurality of separate light signals can be produced by a plurality of separate emitters. The step of combining can include performing wavelength division multiplexing of the light signals. Because the separate light signals have been combined into a single signal, they can be delivered to the tissue under test using a single light guide, as described above.

In yet another aspect of the present invention, a photoplethysmographic measurement apparatus for measuring a blood analyte level in a tissue under test is provided. The apparatus includes: a plurality of emitters, wherein each device produces a light signal having a unique spectral content; a wavelength division multiplexing (WDM) coupler for combining the light signals from the plurality of emitters into a single light signal, wherein the WDM coupler is capable of simultaneously receiving multiple light pulses having unique spectral contents and simultaneously coupling the multiple light pulses onto a single light guide resulting in a single light pulse on the light guide that contains the spectral contents of all of the multiple light pulses; means for delivering the single light signal to the tissue so that the single light signal is directed into the tissue; means for receiving a transmitted light signal from the tissue, the transmitted light signal resulting from the transmission of the single light signal through the tissue; and means for processing the transmitted light signal to determine a blood analyte level in the tissue.

The plurality of emitters can include, as described above, multiple separate light sources, such as light emitting diodes (LEDs) and laser diodes. Alternatively, the plurality of emitters can comprise one or more broadband light sources, such as a tungsten lamp, used with narrowband interference filters to generate multiple narrowband light signals.

The WDM coupler is capable of simultaneously coupling multiple light pulses having different spectral contents onto a single light guide. That is, the WDM coupler is capable of producing a wavelength multiplexed pulse on the single light guide that includes the spectral contents of all of the multiple light pulses. In this regard, the WDM coupler can include any of a number of coupler types, such as those using lenses, prisms, interference filters, diffraction gratings, or butt coupling. In addition, active WDM couplers can also be used.

BRIEF DESCRIPTION OF THE DRAWINGS

FIG. 3 is a diagram illustrating a 4 to 1 coupler arrangement in accordance with one embodiment of the present invention.

DETAILED DESCRIPTION

The present invention relates to a system for performing photoplethysmographic measurements using wavelength division multiplexing. The system is relatively inexpensive to produce and is capable of efficiently and accurately performing photoplethysmographic measurements. The system uses wavelength division multiplexing (WDM) to combine the light signals from multiple light sources in a main test unit into a single multiplexed signal before the signal is delivered to the probe. The multiplexed signal may then be delivered to the probe over a single optical line, such as a single fiber optic cable, a single fiber bundle, or any other single light guide.

Figure 1:
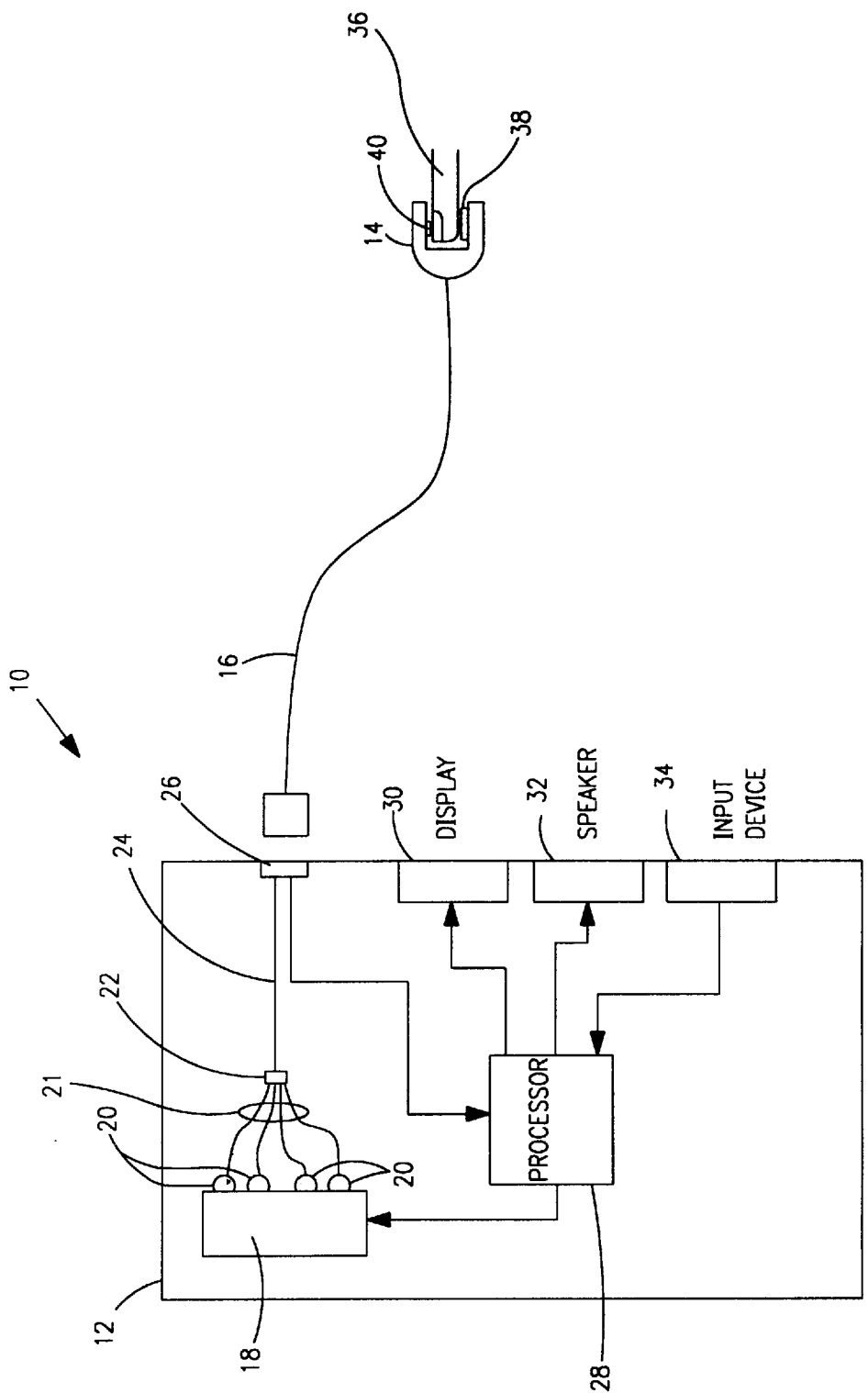
FIG. 1 is a block diagram illustrating a pulse oximetry system in accordance with one embodiment of the present invention.

In one embodiment, as illustrated in FIG. 1, the invention is implemented in a pulse oximetry system 10. The system 10 comprises: a main test unit 12, a probe 14, and a probe cable 16. During a measurement, the probe 14 is first attached to an appropriate appendage of a person being tested, such as finger 36 illustrated in FIG. 1. Light pulses are then delivered from the main test unit 12 to the probe 14 via a single optical transmission line in the probe cable 16. The light pulses are then directed into the finger 36, travel through the finger 36, and emerge on the other side of the finger 36 where they are received by a light pick up device 38. The received light pulses may then be delivered back to the main test unit 12, via probe cable 16, where they are processed to determine the level of one or more blood analytes in the person's arterial blood. Processing methods to determine the blood analyte levels are known and, therefore, will not be discussed further. It should be understood, however, that the benefits of the present invention are independent of the precise method used to measure the analyte levels and, therefore, the invention may be used with virtually any processing method, whether currently known or developed in the future.

Before the light pulses are processed, it is generally required that they be converted to electrical form. This conversion may be performed in the probe, in which case the probe cable includes a thin electrical conductor for carrying the electrical signal back to the main test unit, or it may be performed in the main test unit 12, in which case the light signals are delivered back over the same or a different light transmission line in the probe cable.

The main test unit 12 includes: an emitter module 18 having a plurality of emitters 20, each capable of producing a light signal having a unique spectral content; a plurality of optical cables 21 each coupled to a single emitter source for carrying the corresponding light signal; an optical coupler 22 for coupling light signals from each of the plurality of cables 21 to a single output cable 24; a front panel connector 26 for use in coupling the probe cable 16 to the main test unit 12; a processor unit 28 for performing processing and control functions; a display unit 30 for displaying measurement values to a user; a speaker 32 for providing audible tones to the user; and an input device 34, such as a keypad or a touch screen, for allowing the user to input commands and other information to the processor unit 28.

During operation, the processor unit 28 receives user commands from the input device 34. The processor unit 28 then carries out the commands by controlling the other components in the system 10. For example, the processor unit 28 may receive a command from a user to set alarm limits or to silence an alarm.

To perform an oxygen saturation measurement, the processor unit 28 sends a signal to the emitter unit 18 causing the emitters 20 to produce their corresponding light signals. The emitters 20 may include, for example, laser diodes or light emitting diodes (LEDs). In addition, in one embodiment of the invention, the plurality of emitters includes one or more broadband light sources and appropriate filtering means. As used herein, the term "light emitting diode" includes both infrared emitting diodes and ultraviolet emitting diodes. The light signals are combined in the optical coupler 22 into a single multiplexed light signal on output cable 24. Output cable 24 delivers the multiplexed signal to front panel connector 26 from which it is launched onto a single optical light guide within probe cable 16. Probe cable 16 delivers the multiplexed light signal to the probe 14, from which it is directed into the test subject's finger 36. After the multiplexed light signal has been transmitted through the finger 36, it is returned to the main test unit 12 via probe cable 16 in either optical or electrical form.

To perform photoplethysmographic measurements, light sources must be used that are each capable of producing relatively narrow band light having a unique spectral content. As described above, some light sources capable of performing this function are, for example, light emitting diodes and laser diodes. It is also possible to use a single broadband light source in combination with a number of narrow band filters, although this technique has a number of distinct disadvantages which make it a suboptimal solution.

The optical coupler 22 may comprise any type of device capable of receiving individual light signals from multiple sources and combining them into a single multiplexed signal. In this regard, any of a number of different types of wavelength division multiplexing (WDM) couplers may be used, such as WDM couplers using lenses, prisms, interference filters, diffraction gratings, or butt coupling. Also, active WDM couplers can be used, such as those including cascaded or parallel emitters on a single substrate. Wavelength division multiplexing refers to any method whereby multiple light signals having unique and substantially non-overlapping spectral contents are coupled onto a common light guide. The individual components of the multiplexed signal can then be separated back out by any of a number of methods.

In accordance with the present invention, time division multiplexing (TDM) may also be used in creating the single multiplexed light signal. Time division multiplexing refers to a technique where multiple signals are allowed to share a common transmission means by assigning a unique time slot or channel to each signal. In the present system, TDM can be implemented by appropriately timing the pulsing of the individual light sources in the plurality of light sources 20. Separation of the signals from the multiplexed signal may be accomplished by simply recognizing the individual time slots.

Figure 2A:
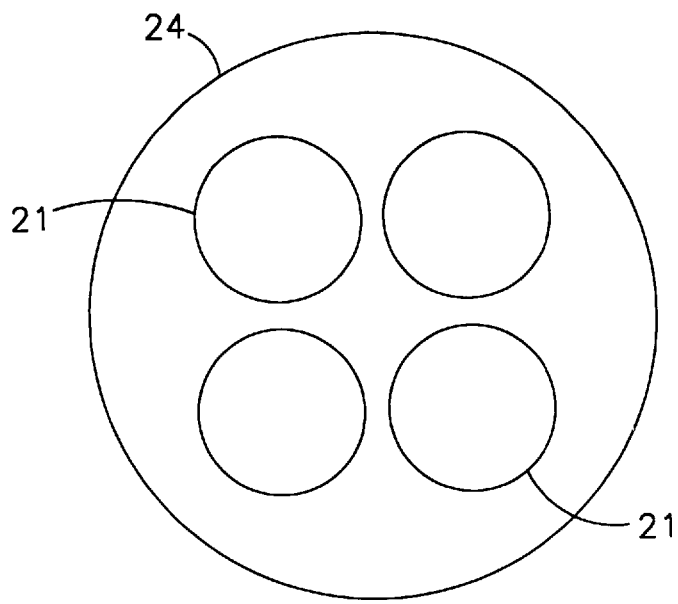
FIGS. 2A and 2B are a front view and a side view, respectively, of a butt coupler in accordance with the present invention.
Figure 2B:
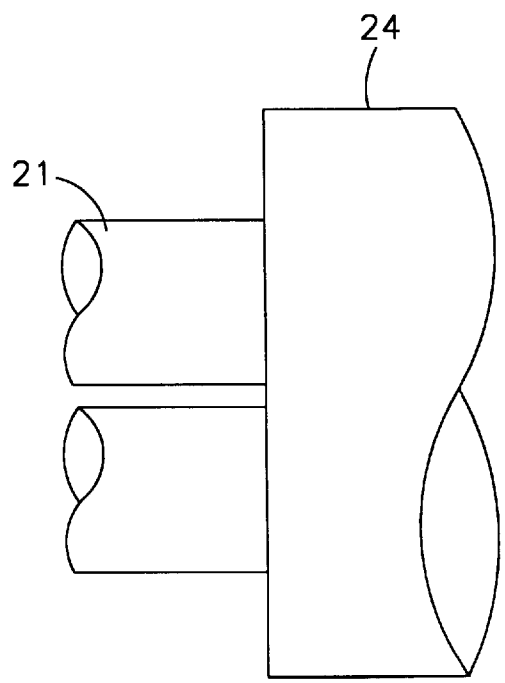

In one embodiment of the present invention, simple butt coupling is utilized in optical coupler 22. As illustrated in FIGS. 2A and 2B, butt coupling comprises butting the ends of each of the plurality of optical cables 21 against the end of the output cable 24. In practice, the smaller diameter cables can be simply held against the end of the larger diameter cable using a mechanical fixture or they can be attached to the larger diameter cable through fusion splicing or adhesive. Butt couplers, such as the one illustrated in FIGS. 4A and 4B, are generally commercially available. One such device, identified as part number US-230, is manufactured by Advanced Custom Application, Inc.

Butt coupling is a preferred coupling method in the present invention because it allows additional input cables to be coupled into the optical circuit relatively easily. For example, if it is determined that another light source is to be added to the system 10 to increase the measurement accuracy of the system 10 or to enable the detection of an additional blood component, the input cable from the new light source can be spliced right into the original butt coupler. Even if no room exists on the end of the output cable 24 for the new input cable, the new cable can be fusion spliced (i.e., melted into) the original coupling using an electric arc or laser fusion welder. Although this technique may lead to unwanted insertion loss being added into the optical circuit, it is a relatively inexpensive method of retrofitting an existing system and does not significantly degrade system performance.

The front panel connector 26 allows the probe cable 16 to be easily removed for storage, transport, or replacement purposes. These types of connectors are commercially available and are usually relatively low-loss. FIG. 3 is a diagram illustrating an emitter coupler configuration in accordance with one embodiment of the present invention. The configuration includes a plurality of laser diodes 42, a plurality of device mounts 44, and coupler unit 46, and a front panel connector 48. The laser diodes 42 each include multiple input leads for inputting electrical control signals. The device mounts 44 are each adapted to receive a single laser diode 42 and to align the diode with a multimode connector 50 in the coupler unit 46. The device mounts 44 are generally available off the shelf, such as part number 501474-1 manufactured by Amp. The multimode connectors 50 feed a plurality of input optical fibers 52 that are coupled into a single output fiber 54. The output fiber 54 is coupled to another multimode connector 56 that is removably insertable into the front panel connector 48 for alignment with an external probe cable. In a preferred embodiment, the input optical fibers 52 are 125/140 um fibers and the output optical fiber is a 400/500 um fiber. The front panel connector can include, for example, part number 501381-1 manufactured by Amp.

As described above, probe cable 16 includes a single light guide for delivering the multiplexed light signal to the probe 14. The optical light guide may include, for example, a single fiber optic cable, a fiber bundle or any other type of light guide. A fiber bundle consists of a multitude of small diameter fibers bundled together to form a single transmission line. Fiber bundles are generally more flexible than single cables having similar dimensions. In addition, fiber bundles may include a large diameter "core", although this generally results in a large loss in flexibility. The term "light guide" refers to any type of optical transmission line including: fiber optic cables, fiber bundles, plastic fibers, plexiglass guides, and liquid core light guides.

In addition to the optical light guide that carries the light pulses to the probe 14, the probe cable 16 must also provide a path for the transmitted light pulses to travel back to the main test unit 12, for processing by the processor unit 28. As described above, the transmitted light pulses may be delivered back optically or electrically. If electrical transmission is used, the probe cable 16 includes conductive means, such as thin wires, for carrying the electrical signal. If optical transmission is used, the probe cable 16 may include a second optical light guide for transferring the transmitted pulses.

The probe 14 includes means for directing the multiplexed light signal into the tissue under test (i.e., finger 36). In its simplest form, the means for directing consists of a structure for holding an end of the appropriate optical light guide adjacent to finger 36 while the probe 14 is properly positioned on the finger 36. For example, if the optical light guide is a fiber optic cable, the probe 14 can include mechanical fixturing for holding the cable so that an end of the cable is substantially flush with the base of the fingernail of the finger 36 and so that the light is directed into the finger. In one embodiment of this invention the light guide is actually brought into the probe parallel to the long axis of the finger and a miniature mirror is used to reflect the light 90 degrees down into the finger.

The probe 14 also includes means for receiving the multiplexed light signal after it has been transmitted through the finger 36. In one embodiment, the means for receiving may include a photodetector, such as a pin or avalanche photodiode, for detecting the transmitted light signal and for converting it to an electrical signal. In another embodiment, the means for receiving may include means for coupling the transmitted light signal into the end of a return optical light guide. In one embodiment, this is accomplished by simply holding an end of the return cable against an opposite side of the finger 36. Because the functions performed by the probe 14 are not structurally demanding, the probe 14 can be constructed of a relatively lightweight, inexpensive material, such as plastics or cloth. In addition, because the probe 14 does not include any light sources, it can be relatively small in size, does not necessarily have to include heat shielding, and can potentially be inexpensive to manufacture.

Although the present invention has been described in conjunction with a preferred embodiment, it is to be understood that modifications and variations may be resorted to without departing from the spirit and scope of the invention as those skilled in the art readily understand. Such modifications and variations are considered to be within the purview and scope of the invention and the appended claims.

What is claimed is:

1. A photoplethysmographic measurement apparatus for measuring a blood analyte level in a tissue under test, comprising:
   a plurality of separate emitters, wherein each emitter produces a light signal having
   a unique spectral content and comprises one of the following: a laser diode and a light emitting diode (LED);
   a plurality of fiber optical elements, each of said elements being associated with one of said emitters so as to carry a corresponding one of said light signals;
   coupling means, associated with each of said plurality of fiber optical elements, for optically coupling each of said elements with a corresponding one of said emitters, each said coupling means comprising axial alignment means for engaging an end portion of one of said fibers such that an end of said fiber is disposed in close proximity to and in axial alignment with a corresponding one of said emitters such that a light signal transmitted by said corresponding one of said emitters is efficiently conveyed into said fiber;
   means for combining said light signals carried by said plurality of elements into a single light signal, said means for combining including means for performing wavelength division multiplexing (WDM);
   means for delivering said single light signal to the tissue so that said single light signal is directed onto the tissue;
   means for receiving a transmitted light signal from the tissue, said transmitted light signal resulting from the transmission of said single light signal through said tissue; and
   means for processing said transmitted light signal to determine a blood analyte level in the tissue.

2. The apparatus, as claimed in claim 1, wherein:
   said means for combining includes means for receiving said light signals from said plurality of emitters and means for coupling said light signals onto a single light guide.

3. The apparatus, as claimed in claim 1, wherein:
   said means for performing wavelength division multiplexing includes a WDM coupler.

4. The apparatus, as claimed in claim 3, wherein:
   said WDM coupler includes at least one of the following: a butt coupling, a lens, a prism, and a diffraction grating.

5. The apparatus, as claimed in claim 1, wherein said means for delivering includes a single light guide for delivering said single light signal to the tissue.

6. The apparatus, as claimed in claim 5, wherein:
   said single light guide includes one of the following:
      a single optical fiber, a single optical fiber bundle, a single plastic fiber, a single plexiglass guide, and a single liquid core guide.

7. The apparatus, as claimed in claim 5, wherein:
   said means for delivering includes a probe head, coupled to a distal end of said single light guide and removably attachable to the tissue for holding said distal end of said single light guide in a relatively fixed position with respect to said tissue during a measurement.

8. The apparatus, as claimed in claim 7, further comprising:
   a housing carrying said plurality of emitters and said means for combining, wherein said probe head is physically separate from said housing and said single light guide extends between said housing and said probe head.

9. The apparatus, as claimed in claim 1, wherein;
   said blood analyte level includes an oxygen saturation level in said living tissue.

10. The apparatus, as claimed in claim 1, wherein: said blood analyte level includes the concentration of oxyhemoglobin and carboxyhemoglobin.

11. The apparatus, as claimed in claim 1, wherein:
   said blood analyte level includes the concentration of oxyhemoglobin, carboxyhemoglobin, and methemoglobin.

12. A photoplethysmographic measurement apparatus for measuring a blood analyte level in a tissue under test, comprising:
   a plurality of emitters, wherein each emitter produces a light signal having a unique spectral content;

a plurality of light guides associated with said plurality of emitters and having a light guide for each of said plurality of emitters for receiving and carrying a corresponding light signal;

coupling means for receiving said plurality of emitters and for axially aligning each of said plurality of emitters with a corresponding one of said plurality of light guides such that an end of each of said light guides is disposed in close proximity to and in axial alignment with a corresponding one of said plurality of emitters, wherein light is efficiently communicated between said emitters and said light guides;

wavelength division multiplexing (WDM) coupler, coupled to said plurality of light guides, for receiving said light signals from said light guides and combining said light signals into a single light signal;

means for delivering said single light signal to the tissue so that said single light signal is directed into the tissue;

means for receiving a transmitted light signal from the tissue, said transmitted light signal resulting from the transmission of said single light signal through said tissue; and means for processing said transmitted light signal to determine a blood analyte level in the tissue.

13. The apparatus, as claimed in claim 12, wherein:

said plurality of light guides includes at least one of the following: an optical fiber and a fiber bundle.

14. The apparatus, as claimed in claim 13, wherein:

said plurality of light guides includes a separate light guide for each of said plurality of emitters.

15. A photoplethysmographic measurement apparatus for measuring a blood analyte level in a tissue under test, comprising:

a plurality of emitters, wherein each emitter produces a light signal having a unique spectral content;

a wavelength division multiplexing (WDM) coupler, coupled to said plurality of emitters, for receiving said light signals from said emitters and combining said light signals into a single light signal, wherein said WDM coupler includes a butt coupling for coupling a plurality of light guides into a single light guide;

means for delivering said single light signal to the tissue so that said single light signal is directed into the tissue;

means for receiving a transmitted light signal from the tissue, said transmitted light signal resulting from the transmission of said single light signal through said tissue; and means for processing said transmitted light signal to determine a blood analyte level in the tissue.

16. A photoplethysmographic measurement apparatus for measuring a blood analyte level in a patient, comprising:

a plurality of individual light sources, each light source producing an optical output signal having a unique spectral content;

a plurality of light guides for receiving said plurality of optical output signals;

source coupling means, associated with each of said plurality of light guides, for optically coupling each of said light guides with a corresponding one of said sources, each said source coupling means comprising axial alignment means for engaging an end portion of one of said light guides such that an end of said light guide is in close proximity to and in axial alignment with a corresponding one of said sources such that a light signal transmitted by said corresponding one of said sources is efficiently conveyed into said light guide:

a coupler, associated with said plurality of light guides, for combining said optical output signals from said plurality of light sources, using wavelength division multiplexing, to create a multiplexed optical signal;

a probe, capable of being removably coupled to an appendage on the patient, for facilitating the transmission of said multiplexed optical signal into said appendage on the patient;

a single input/single output light guide for delivering said multiplexed optical signal from said coupler to said probe;

detection means, coupled to said probe, for detecting said multiplexed optical signal after said multiplexed optical signal has been transmitted through said appendage and for converting said multiplexed optical signal to an electrical signal; and processing means, coupled to said detection means, for processing said electrical signal to determine a composition measurement value;

wherein said plurality of individual light sources, said coupler, and said processing means are located within a housing, separate from said probe, and said light guides extend between said housing and said probe.

* * * * *